United States Patent [19]

Tallafus

[11] Patent Number: 5,193,350
[45] Date of Patent: Mar. 16, 1993

[54] METHOD OF STERILIZING DRIED GOODS

[76] Inventor: Ottmar Tallafus, Am Himmelreich 14, 6967 Buchen 1, Fed. Rep. of Germany

[21] Appl. No.: 690,107

[22] Filed: Apr. 23, 1991

[30] Foreign Application Priority Data

Apr. 24, 1990 [EP] European Pat. Off. ........ 90107746.1

[51] Int. Cl.⁵ .................................................. F25D 17/02
[52] U.S. Cl. .......................................... 62/64; 426/320; 426/524
[58] Field of Search ............................ 62/64, 78, 374; 426/418, 419, 320, 524

[56] References Cited

U.S. PATENT DOCUMENTS

| | | | |
|---|---|---|---|
| 3,768,272 | 10/1973 | Barrett | 62/374 |
| 4,200,656 | 4/1980 | Cohen et al. | 426/320 |
| 4,827,727 | 5/1989 | Caracciolo | 62/78 |
| 5,027,546 | 7/1991 | Tallon | 62/64 |

*Primary Examiner*—Ronald C. Capossela

[57] ABSTRACT

In a method of sterilizing dry goods such as herbs, spices and teas, the goods are exposed in a closed containment to a refrigerant and cooled to below minus 20° C. thereby to destroy any living organisms as well as the larvae and eggs thereof. The process achieves a total mortality rate for the organisms and the larvae and eggs utilizing relatively inexpensive apparatus and environmentally safe refrigeration materials, preferably liquid cold gases such as liquid nitrogen, liquid carbon dioxide and liquid air.

9 Claims, 2 Drawing Sheets

METHOD OF STERILIZING DRIED GOODS

BACKGROUND OF THE INVENTION

The invention relates to a method of sterilizing dried good such as dried herbs, spices, teas, drugs and remedies by introducing a gas into a sealed container receiving the goods for destroying adult organisms as well as larvae and eggs thereof.

In an article by the authors Egon Stahl, G. Rau and H. Adolphi printed in the magazine "Die Pharmazeutische Industrie" (Pharm. Ind. 47, 5, 528 to 530 (1985)), the following is stated: "To some degree drugs (herbs) are always contaminated by harmful insects, larvae or eggs. As agents for destroying the insects, larvae and eggs, phosphine, ferrocyanide and methylbromide are utilized. Use of these gases is limited however because they are poisonous and because residues remaining within the goods generate metabolites. Ethylene oxide which has frequently been used until recently has now been found to be carcinogenic and has been outlawed as a pesticide and also as a disinfectant.

Other methods such as gamma irradiation and steam sterilization or treatment with alcohol vapors result in detrimental changes in the treated drugs."

The authors further state that, for hygienic economical reasons, sterilization of the drugs is absolutely necessary and that, therefore, they have been searching for a new process. At that point of time a pressure/expansion method was found to be optimal for pressure sterilization of foods and medicinal plants. As described in another article of the authors W. Pohlen, G. Rau and E. Finkenzeller in the magazine "Die Pharmazeutische Industrie" (Pharm. Ind. 51, 8, 917–918 (1989)) this method is utilized as follows:

"The material to be treated may remain in the original package and is transported into a pressure autoclave on an especially designed transport cart. When completely filled the autoclave is closed. In order to avoid exposure of the drugs to oxygen the autoclave may be evacuated by means of a vacuum pump to a residual pressure of about 200 m bar. Gaseous carbon dioxide is admitted to the pressure chamber from a storage container by means of a control arrangement until the desired final pressure—according to the article 18 bar to 25 bar—is reached. After the required exposure period the carbon dioxide is released. After complete pressure equilization the autoclave is opened and the treated goods are removed."

The mortality rate for damaging insects as a result of this pressure/expansion procedure was in fact found to be 100% to almost 100%. The disadvantage of this method is that not all the insects are destroyed all the time, particularly not their larvae and eggs and that the process requires expensive apparatus and equipment.

It is therefore the object of the present invention to provide a method for the sterilization of dried goods of the type described wherein all damage-causing insects as well as their larvae and eggs are safely destroyed and which may be utilized economically without the need for expensive apparatus which require large investments.

SUMMARY OF THE INVENTION

A method of sterilizing dried goods such as herbs, spices, teas and herbal remedies, wherein the goods are introduced into a containment in which they are exposed to a refrigerant and cooled to below minus 20° C. thereby to destroy any living organisms as well as any larvae and eggs thereof. Preferably a liquid cold gas is utilized as a refrigerant, that is, a low temperature liquid which is gaseous under normal temperature conditions, such as liquid nitrogen, liquid carbon dioxide or liquid air, to which the goods are directly exposed in the containment. The goods may remain packaged and the process may be performed in a continuous manner by passing the goods through a refrigeration tunnel.

It has been found that, by this process, a total mortality rate can be achieved for the living organisms as well as for the larvae and eggs thereof and the process can be performed with relatively inexpensive apparatus since it can be performed at atmospheric pressure.

The insects and their larvae and eggs are destroyed by exposure to low temperatures, that is, to temperatures below minus 20° C., in order to achieve a perfect mortality rate for the damage-causing organisms or insects and their larvae and eggs. The reason for this is mainly that cells of the adult insects and of the larvae and eggs are destroyed by their exposure to low temperature and also as a result of the effects of the gases used for cooling on the breathing functions of the insects. As mentioned however the primary reason for the good results is believed to be the low temperature exposure which may be taken from a mortality curve-temperature/time. As tests have shown, all damage-causing insects including their larvae and eggs are destroyed after a very short period of seconds or minutes if they are exposed to very low temperature, for example, by immersion of the goods directly into a liquid cold gas. With increasing temperature a longer exposure time is required to achieve total mortality. The mortality curve approaches asymptotically a minus 20° C. temperature line which means that the temperature should be lower than minus 20° C. Another limitation is presented by the adaptability particularly of the larvae and eggs which limit is about 24 hours. It has been found that the organisms showed less low temperature sensitivity when exposed to low temperature for longer than 24 hours as a result of some kind of an adaptation process.

In spite of the fact that the mechanism by which the organisms are destroyed has not yet been fully understood, utilization of the sterilizing process according to the invention has shown that the objects of the invention are being met, specifically, a 100% mortality rate is achieved.

As far as the economic aspects are concerned it is pointed out that already the use of unpressurized containers results in substantially reduced costs for the equipment. Furthermore the method according to the invention may be utilized as a continuous sterilizing process if, in place of a container, a cooling tunnel or a refrigeration auger suitably supplied with a liquid refrigerant is utilized. With regard to the economic aspects it is further pointed out that it is only of secondary importance what kind of refrigerant gas is utilized so that the refrigerant gas that is most easily obtained or most easily utilized can be used. It is also to be taken into consideration that the sterilizing process according to the invention can be performed in a relatively short period of time.

In practice the sterilization method according to the invention may be performed for example by the following steps:

a) Introducing the goods packaged as supplied into a heat insulated container, b) Closing of the container and introducing a liquid cold gas into the container, c) Maintaining the goods in the container refrigerated until the desired low temperature is obtained in center of the goods packages, and d) Removal of the sterilized goods from the container.

As mentioned earlier, in place of the container, a rapid-freeze cell or a refrigerating tunnel or an immersion bath with a liquid cold gas or a corresponding cooling auger may be utilized. If a container is used it should be provided with a discharge valve suitably mounted on the container such that, after the air is discharged by admission of the refrigerant gas, the valve can be closed to such a degree that the container is slightly pressurized in order to prevent infiltration of air.

BRIEF DESCRIPTION OF THE DRAWINGS

FIG. 1 shows the required cold gas exposure time required for sterilization of the goods depending on the temperature obtained in the center of a package of such goods. It can be seen that sterilization can be achieved within seconds if the goods are exposed directly to liquid refrigerant gas (liquid nitrogen) but that, with a core temperature for the package of minus 25° C., an exposure time of about four hours is required.

Figure 1:
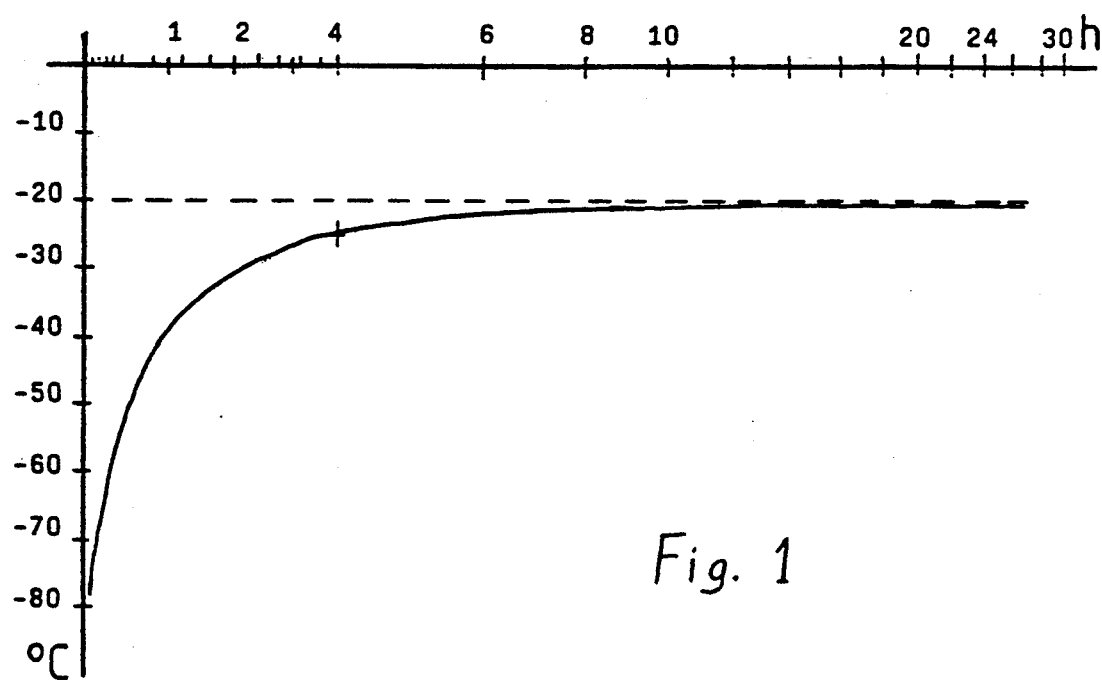
FIG. 1 is a graph indicating required cold gas exposure time for the dried goods, FIG. 2 schematically shows a container in which the dried goods are exposed to refrigerant, FIG. 3 schematically shows a refrigerant tunnel for the dried goods, FIG. 4 schematically shows a liquid refrigerant tank for receiving and rapidly cooling the dried goods, and FIG. 5 schematically shows a refrigerant tank with an auger for removing the dried goods.
Figure 2:
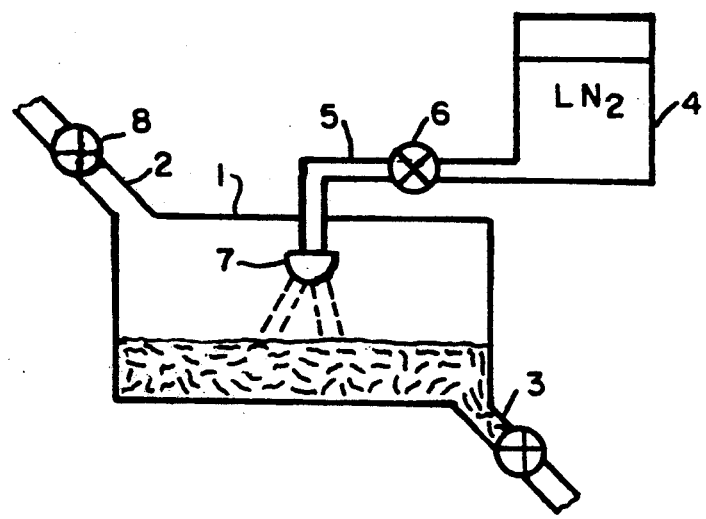
FIG. 2 shows a container 1 in the form of a closed housing having an inlet 2 and an outlet 3 for the dried goods. A liquid refrigerant tank 4 is in communication with the container 1 via a supply line 5 provided with a refrigerant valve 6 and a spray head 7 at its end within the container 1. The inlet 2 and outlet 3 include valves 8 and 9 which can be closed to maintain the container and slight pressure.
Figure 3:
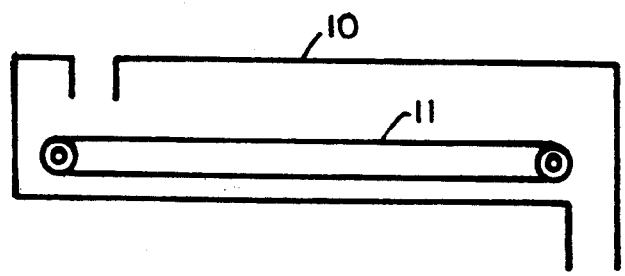
FIG. 3 shows schematically a refrigeration tunnel 10 through which a conveyor 11 extends for carrying the dried goods through the tunnel at a speed sufficiently slow to appropriately cool the dried goods.
Figure 4:
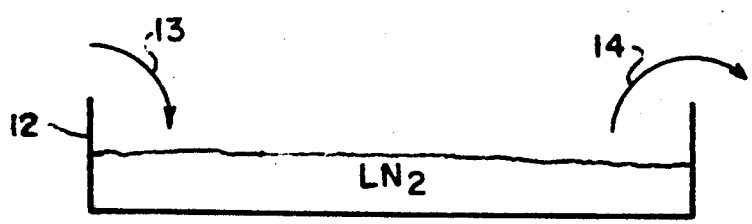
As shown in FIG. 4 a liquid refrigerant filled container 12 may be provided into which the dried good is dipped for the required exposure time. The arrows 13 and 14 indicate the dipping and retrieving of the dried goods.
Figure 5:
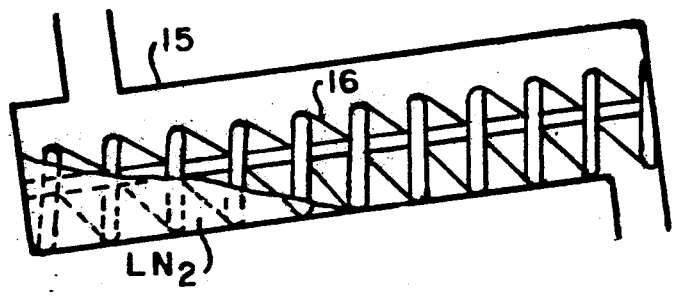
As shown in FIG. 5 this can be accomplished by providing an inclined container 15 with an auger structure 16 which carries the dried goods out of the $LN_2$ bath 17 in the lower end of the container to a discharge opening 18 at the upper end of the inclined container.

What is claimed is:

1. A method of sterilizing dried goods, such as dried herbs, spices, teas, and remedies, comprising the steps of introducing the goods into a container, and introducing into the container a refrigerant with a temperature of less than minus 20° C., retaining the dried goods in said container at least until the entire content of said container reaches a temperature of less than minus 20° C. thereby to destroy any adult organisms as well as the larvae and eggs thereof.

2. A method according to claim 1, wherein as said refrigerant liquid and/or gaseous carbon dioxide ($LCO_2/CO_2$) is introduced into said container.

3. A method according to claim 1, wherein as said refrigerant liquid and/or gaseous nitrogen ($LN_2/N_2$) is introduced into said container.

4. A method according to claim 1, wherein as said refrigerant liquid and/or gaseous air is introduced into said container.

5. A method according to claim 1, comprising the steps of
    a) introducing the dried goods, disposed within packages, into an insulated container,
    b) closing the container and introducing a refrigerant into the container,
    c) leaving the goods in the container until a predetermined low temperature is achieved within the center of the goods in the packages, and
    d) removing the then sterilized packaged goods from the container.

6. A method according to claim 5, wherein said dried goods are exposed to said refrigerant in a refrigeration tunnel through which said dried goods are moved.

7. A method according to claim 5, wherein said dried goods are dipped into a tank filled with a liquid cold gas.

8. A method according to claim 5, wherein said goods are moved through said container by an auger having a feed end filled with a liquid cold gas.

9. A method according to claim 5, wherein, after introduction of the refrigerant into the container, a gas discharge valve associated with the contain is closed to such a degree that the container remains slightly pressurized.

* * * * *